US008683996B2

(12) United States Patent
Allen et al.

(10) Patent No.: US 8,683,996 B2
(45) Date of Patent: *Apr. 1, 2014

(54) LIFE SUPPORT AND MICROCLIMATE INTEGRATED SYSTEM AND PROCESS

(75) Inventors: Jeffrey Allen, Hamburg, NY (US); Ian Archer, Williamsville, NY (US); Kevin Kankolenski, Clarence Center, NY (US); Manus Michael O'Donnell, Hamburg, NY (US); Lucas Mesmer, Grand Island, NY (US)

(73) Assignee: Carleton Technologies, Inc., Orchard Park, NY (US)

( * ) Notice: Subject to any disclaimer, the term of this patent is extended or adjusted under 35 U.S.C. 154(b) by 252 days.

This patent is subject to a terminal disclaimer.

(21) Appl. No.: 12/931,071

(22) Filed: Jan. 24, 2011

(65) Prior Publication Data

US 2011/0184252 A1 Jul. 28, 2011

Related U.S. Application Data

(60) Provisional application No. 61/297,725, filed on Jan. 22, 2010, provisional application No. 61/318,387, filed on Mar. 29, 2010.

(51) Int. Cl.
| | | |
|---|---|---|
| A61F 7/08 | (2006.01) | |
| A61F 7/02 | (2006.01) | |
| A61F 7/00 | (2006.01) | |
| A61M 16/14 | (2006.01) | |
| A61M 16/10 | (2006.01) | |
| A61M 16/00 | (2006.01) | |

(52) U.S. Cl.
CPC .............. *A61F 7/0085* (2013.01); *A61F 7/08* (2013.01); *A61F 7/0097* (2013.01); *A61F 7/0053* (2013.01); *A61F 7/00* (2013.01); *A61M 16/14* (2013.01); *A61M 16/10* (2013.01); *A61M 16/00* (2013.01); *A61F 2007/0054* (2013.01)
USPC ............ 128/204.17; 128/204.15; 128/202.19; 128/202.11; 128/201.23; 128/201.22; 128/200.24; 607/104

(58) Field of Classification Search
USPC ............. 128/200.24, 201.13, 201.22, 201.27, 128/202.11, 202.12, 202.13, 202.19, 128/205.26; 600/21, 22, 19, 20; 601/18–152; 602/27, 13, 75; 126/204; 405/185–187; 607/104
See application file for complete search history.

(56) References Cited

U.S. PATENT DOCUMENTS

| | | | |
|---|---|---|---|
| 3,049,896 A * | 8/1962 | Webb ........................ | 128/201.25 |
| 3,079,765 A | 3/1963 | Le Vantine | |
| 3,179,360 A | 4/1965 | Shelton et al. | |
| 3,463,150 A | 8/1969 | Penfold | |
| 3,635,216 A * | 1/1972 | Curtis ....................... | 128/202.11 |
| 3,648,289 A * | 3/1972 | Moreland ................ | 128/201.27 |
| 3,667,459 A * | 6/1972 | Durney .................... | 128/201.15 |
| 3,730,178 A * | 5/1973 | Moreland ................ | 128/201.21 |
| 3,751,727 A | 8/1973 | Shepard et al. | |
| 3,869,871 A * | 3/1975 | Rybalko et al. ................. | 62/178 |
| 3,884,216 A * | 5/1975 | McCartney ................... | 126/204 |
| 4,013,122 A * | 3/1977 | Long ............................. | 165/154 |

(Continued)

*Primary Examiner* — Annette Dixon

(74) *Attorney, Agent, or Firm* — Jaeckle Fleischmann & Mugel, LLP

(57) ABSTRACT

The present invention of one embodiment includes a combined microclimate, thermal management, life-support system for care of patient and system for measurement of vital signs. The system of one embodiment, provides active external heating and simultaneously provides active internal heating.

21 Claims, 6 Drawing Sheets

(56) References Cited

U.S. PATENT DOCUMENTS

| | | | |
|---|---|---|---|
| 4,024,730 A * | 5/1977 | Bell et al. ..................... 62/259.3 |
| 4,172,454 A * | 10/1979 | Warncke et al. ......... 128/201.29 |
| 4,195,619 A * | 4/1980 | Hollen .......................... 126/204 |
| 4,352,991 A | 10/1982 | Kaufman |
| 4,620,537 A * | 11/1986 | Brown ..................... 128/201.13 |
| 4,708,831 A * | 11/1987 | Elsworth et al. .............. 261/130 |
| 4,739,913 A | 4/1988 | Moore |
| 4,741,332 A * | 5/1988 | Beaussant ................ 128/201.23 |
| 5,127,896 A * | 7/1992 | de Gaston ....................... 600/20 |
| 5,179,746 A | 1/1993 | Rogers |
| 5,259,372 A | 11/1993 | Gross et al. |
| 5,279,287 A * | 1/1994 | Wiseman, Sr. ........... 128/201.29 |
| 5,309,901 A * | 5/1994 | Beaussant ................ 128/202.12 |
| 5,318,018 A * | 6/1994 | Puma et al. .............. 128/202.11 |
| 5,421,326 A * | 6/1995 | Rankin et al. ............ 128/201.19 |
| 5,477,850 A * | 12/1995 | Zegler et al. ............. 128/202.11 |
| 5,572,880 A * | 11/1996 | Frustaci et al. ............... 62/259.3 |
| 5,626,151 A * | 5/1997 | Linden .......................... 128/897 |
| 5,975,081 A | 11/1999 | Hood et al. |
| 6,418,932 B2 | 7/2002 | Paschal, Jr. et al. |
| 6,432,124 B1 * | 8/2002 | Worthen et al. ............... 607/105 |
| 6,899,103 B1 * | 5/2005 | Hood et al. .................... 128/845 |
| 7,087,075 B2 * | 8/2006 | Briscoe et al. ................ 607/104 |
| 7,179,279 B2 * | 2/2007 | Radons et al. ................ 607/108 |
| 7,503,809 B2 | 3/2009 | Tsai et al. |
| 2008/0060101 A1 | 3/2008 | Cadogan |

* cited by examiner

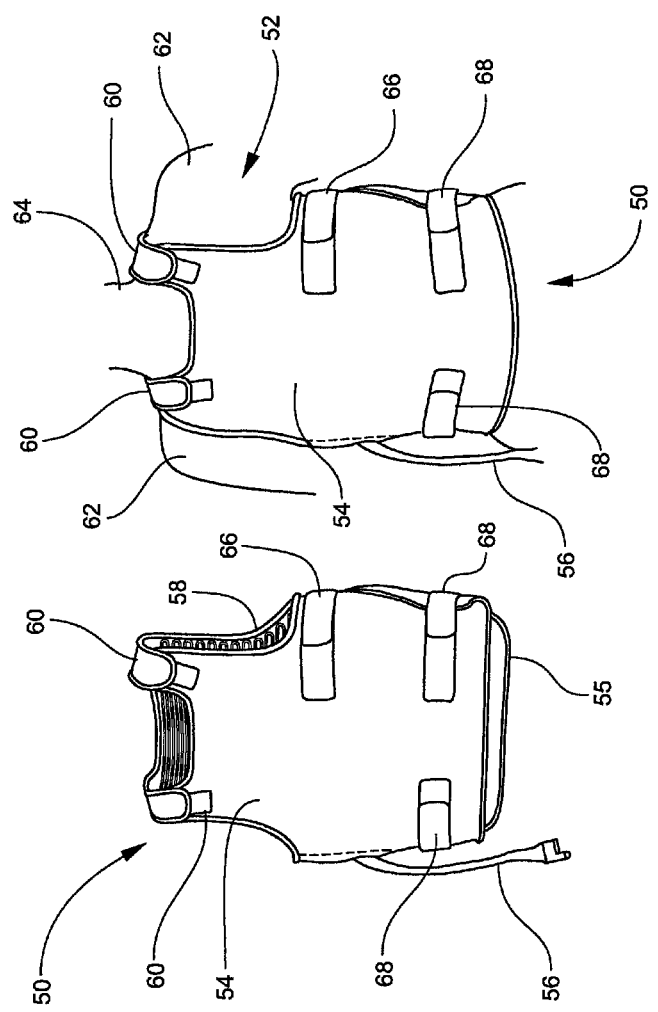

LIFE SUPPORT AND MICROCLIMATE INTEGRATED SYSTEM AND PROCESS

CROSS-REFERENCE TO RELATED APPLICATIONS

This application claims the benefit of U.S. Provisional Application No. 61/297,725 filed Jan. 22, 2010 and U.S. Provisional Application No. 61/318,387 filed Mar. 28, 2010, which applications are incorporated herein by reference.

BACKGROUND OF THE INVENTION

1. Field of Invention

This invention relates generally to portable systems and processes for emergency life-support and thermal regulation of patients from the point of injury to hospital, and more particularly to portable systems and processes for emergency life-support and thermal regulation of patients from point of injury to hospital in military operations.

2. Discussion of Related Art

Military medical personnel cite that greater than 20% of combat casualties could be avoided if medical care was available at the point of injury. The 3 primary front line medical needs they identify are (1) blood preservation by either preventing blood loss or making blood more readily available, (2) treatment of hypothermia through internal (warmed oxygen inhalation) and external heating (heated garments, pad, blankets or bags), (3) respiration therapy through oxygen treatment. Additional research indicates that illness and disease can be managed by having an available means to reduce body temperature. Induced hypothermia research is also now underway as a possible means to slow body metabolism to slow the rate of blood loss.

In addition to the treatment of patients in cold conditions, there is a need to maintain patients in a cool environment when patients that have suffered from heat related casualties in extreme hot environments such as, for example, the Iraqi desert in summer.

Existing technology employs individual hardware such as a heater, a blood refrigerator, an IV warmer, an oxygen supply system, an oxygen warmer, and vital sign sensors and monitors. These technologies are not available to the first responder in one inclusive system. The collection of these individual stand alone components take up a large space and are heavy, preventing it from being portable or effective for front line responders. These individual technologies are typically designed for hospital settings and not designed for use in the harsh environment required by the military.

There exists a need for an integrated system that incorporates various life-support, patient monitoring and thermal regulating functions to create a desired microclimate for the patient. There is a need for such a system that is lightweight, robust and compact which enables it to be used effectively by front-line medical responders. The present invention addresses one or more of these and other needs.

SUMMARY OF THE INVENTION

The present invention includes a portable microclimate and life-support system for care of a patient. The system is small enough and light enough to be carried by one person. It is a stand alone unit that provides the ability to treat both therapeutically and prophylactically hypothermia and hyperthermia via a thermal regulated body covering that is actively heated or cooled (depending upon the therapeutic or prophylactic treatment) by a thermal fluid supplied from the microclimate and life support system. Generally, the system of the present invention measures and displays vital signs of a patient including body temperature, blood oxygen levels and heart rate. In another embodiment, the system measures and displays the temperature of the thermal fluid before it enters the thermal fluid passages of the body covering and the oxygen temperature of the body.

An oxygen supply is provided to help prevent, protect against, or help facilitate recovery from hypoxia, hyperventilation or shock. Optionally, the oxygen supply is heated so that when a patient is treated for hypothermia, the oxygen supply can provide internal active heating to the patient. The system of one embodiment of the present invention is configured to provide active heating, both internally and externally at the same time. Such a treatment is believed to provide faster and improved recovery from hypothermia.

Likewise, the oxygen supply can be cooled so that when a patient is treated for hyperthermia, the oxygen supply can provide internal active cooling to the patient. The system of one embodiment of the present invention is configured to provide active cooling, both internally and externally at the same time. Such a treatment is believed to provide faster and improved recovery from hyperthermia. In one aspect of the invention the oxygen unit is configured to reduce moisture loss from breathing.

The present invention is lightweight, efficient and portable. In one embodiment, the weight is a maximum of about 60 pounds, about 55 pounds, about 50 pounds, or about 45 pounds. The system is capable of delivering external thermal fluid, delivering oxygen and displaying one or more vital signs for a period that is a minimum of about 1 hour, about 1.5 hours, or about 2 hours. The present invention is capable of treating hyperthermia in at ambient temperatures that are a minimum of 55 degrees Fahrenheit and a maximum of 150 degrees Fahrenheit. The present invention is capable of treating hyperthermia ambient temperatures that are a minimum of 0 degrees Fahrenheit and a maximum of 95 degrees Fahrenheit.

The patient is actively heated by a body covering that has one or more thermal conduits through witch a thermal fluid passes to actively heat or cool the patient. To improve efficiency the thermal covering is made of an elastic material and has fasteners—preferably around the proximity of the body covering such that the body covering better conforms to the user's torso better than the prior art. This will provide closer proximity thermal contact between the cooling/heating fluid and the user's torso or clothing—increasing thermal efficiency.

In one embodiment of the present invention there is a portable microclimate and life support system. The system comprises a portable housing that houses therein (i) a heat exchanger configured to regulate the temperature of a thermal fluid, (ii) an oxygen source, and (iii) one or more vital sign displays. The heat exchanger has a thermal fluid outlet port and a thermal fluid return port. The system also has a body covering (such as a blanket, a vest, or a bag that is configured to be placed in covering contact with the patient. The body covering has one or more thermal fluid passages to regulate the temperature of the patient in thermal contact with the body covering. By thermal fluid it is meant a fluid that heats or cools in a fluid heating or cooling system. By oxygen source, it is meant a source of oxygen suitable for breathing. The oxygen source may be ambient air. It may be ambient air with enhanced amount of oxygen or it may be a purified oxygen source such as an oxygen tank or oxygen from an air scrubber. "Regulate the temperature," as used herein, means to heat or cool a body or object to a desired temperature. Body covering is a covering that provides insulation to the body for the purpose of warming or cooling the body.

The system also comprises a thermal conduit in fluid communication with the one or more thermal fluid passages of the body covering. The thermal conduit has a thermal fluid supply tube in fluid communication with the thermal fluid outlet port and a thermal fluid return tube in fluid communication with the thermal fluid inlet port. The thermal conduit forms a closed fluid loop for delivering thermal fluid from the heat exchanger to the one or more thermal fluid passages and returning thermal fluid from the one or more thermal fluid passages. Additionally, the system has an oxygen delivery interface and an oxygen delivery conduit in fluid communication with the oxygen source. The oxygen delivery conduit is configured to deliver oxygen from the oxygen delivery source to the oxygen delivery interface.

Optionally, the system also has one or more vital sign measurement devices selected from the group consisting of a patient temperature sensor, a patient oximeter; a patient heart rate monitor (including pulse monitors), wherein the one or more vital sign measurement devices is in electromagnetic communication with the one or more vital sign displays. By electromagnetic communication, it is meant that a sensor or measuring device provides an electric or electromagnetic signal to a display unit and/or its processor so that the desired signal can be displayed as a measurement. The portable system is capable of actively thermally regulating a patient, providing oxygen (including ambient air) and simultaneously measuring one or more vital signs.

In one embodiment of the present invention there is a method of therapeutically or prophylactically treating a patient for hypothermia and simultaneously therapeutically or prophylactically treating a patient for a condition selected from the group consisting of hyperventilation, shock or hypoxia. The method comprising the providing a microclimate and life support system according to one or more embodiments disclosed herein. The patient is covered with a body covering comprising a plurality of thermal fluid passages. Heated thermal fluid is delivered to a plurality of thermal fluid passages of a body covering thereby providing active external heat to the patient. The patient is fitted with an oxygen delivery interface in fluid communication with an oxygen source. Oxygen is delivered to the patient from the oxygen source to the respiratory system of the patient. One or more vital signs of the patient are optionally measured.

In one embodiment of the present invention there is a method of therapeutically or prophylactically treating a patient for hyperthermia and simultaneously therapeutically or prophylactically treating a patient for a condition selected from the group consisting of hyperventilation, shock or hypoxia. The method comprising the providing a microclimate and life support system according to one or more embodiments disclosed herein. The patient is covered with a body covering comprising a plurality of thermal fluid passages. Cooled thermal fluid is delivered to the plurality of thermal fluid passages of a body covering thereby providing active external cooling to the patient. The patient is fitted with an oxygen delivery interface in fluid communication with an oxygen source. Oxygen is delivered to the patient from the oxygen source to the respiratory system of the patient. One or more vital signs of the patient are optionally measured.

In one embodiment, there is a portable microclimate and life-support system for care of a patient. The system comprises a portable housing that houses therein (i) a heat exchanger configured to regulate the temperature of a thermal fluid and (ii) an oxygen source. The heat exchanger has a thermal fluid outlet port and a thermal fluid return port. The system includes a body covering configured to be placed in covering contact with the patient having one or more thermal fluid passages to regulate the temperature of the patient in thermal contact with the body covering.

The system further includes a thermal conduit in fluid communication with the one or more thermal fluid passages of the body covering. The thermal conduit has a thermal fluid supply tube in fluid communication with the thermal fluid outlet port and a thermal fluid return tube in fluid communication with the thermal fluid inlet port. The thermal conduit forms a closed fluid loop configured to deliver thermal fluid from the heat exchanger to the one or more thermal fluid passages and returning thermal fluid from the one or more thermal fluid passages. The system further includes an oxygen delivery interface and an oxygen delivery conduit having an oxygen heating source in thermal communication with at least a part of the length of the oxygen delivery conduit. The oxygen thermal regulating source is configured to thermally regulate the oxygen in the oxygen delivery conduit. In one embodiment, the oxygen thermal regulator is configured to heat the temperature of oxygen to a temperature above the core temperature of the patient. The oxygen delivery conduit is in fluid communication with the oxygen delivery source and is configured to deliver oxygen from the oxygen delivery source to the oxygen delivery interface. By oxygen delivery interface it is meant a device that interfaces with a patient's body to provide oxygen or air.

In one embodiment there is a method of therapeutically or prophylactically treating a patient for hypothermia, and simultaneously therapeutically or prophylactically treating a patient for a condition selected from the group consisting of hyperventilation, shock or hypoxia. The method comprising the steps of providing a microclimate and life support system of one or more embodiments disclosed herein. According to one embodiment, a body covering having one or more thermal fluid passages is placed in covering contact with a patient. A heated thermal fluid is delivered to the plurality of thermal fluid passages of the body covering thereby providing external active heat to the patient. The patient is fitted with an oxygen delivery interface and heated oxygen from the oxygen source is delivered to provide active internal heat to the patient.

In one embodiment there is a method of therapeutically or prophylactically treating a patient for hyperthermia, and simultaneously therapeutically or prophylactically treating a patient for a condition selected from the group consisting of hyperventilation, shock or hypoxia. The method comprising the steps of providing a microclimate and life support system of one or more embodiments disclosed herein. According to one embodiment, a body covering having one or more thermal fluid passages is placed in covering contact with a patient. A cooled thermal fluid is delivered to the plurality of thermal fluid passages of the body covering thereby providing external active cooling to the patient. The patient is fitted with an oxygen delivery interface. Cooled oxygen from the oxygen source is delivered to provide active internal cooling to the patient.

In one embodiment, the system optionally comprises a thermal fluid temperature sensor configured to measure the thermal fluid temperature prior to the thermal fluid entering the one or more thermal fluid passages of the thermal cover, wherein the thermal fluid temperature is displayed in a thermal temperature display on the portable housing. The invention of one embodiment includes a method of treating a patient that comprises measuring the thermal fluid temperature prior to the thermal fluid entering the one or more thermal fluid passages and displaying the temperature in a vital signs display. The method further includes the step of adjusting the temperature of the thermal fluid in response to the step of measuring the thermal fluid temperature.

In another embodiment, the system further comprises an oxygen temperature sensor configured to measure the oxygen temperature in or upstream from the oxygen delivery interface. The thermal fluid temperature is displayed in a thermal temperature display on the portable housing. The invention of one embodiment includes a method of treating a patient that comprises measuring the oxygen temperature in or upstream from the oxygen delivery interface and displaying the temperature in a vital signs display. The method further includes the step of adjusting the temperature of the oxygen in response to the step of measuring the oxygen temperature.

In still another embodiment, the housing is capable of being carried by one person. Preferably the housing is capable of being carried on a person's back. Optionally, the housing is capable of being mounted on a shock absorbing vehicle mount.

In one embodiment, the portable housing has a maximum weight of about 60 pounds, about 55 pounds, about 50 pounds, or about 45 pounds. In another embodiment, the portable housing is a maximum of about 1.5 cubic feet, or about 1 cubic feet.

In yet another embodiment, the body covering is made of an elastic fabric material and further comprises fasteners configured to fasten the body covering to the patient. The elastic material conforms itself to the contour of the patient's body. In one preferred embodiment, the fastener is a hook and loop fastener. The fasteners are attached to the perimeter of the body covering.

In still another embodiment, the body covering is a blanket, a bag or clothing garment.

In yet another embodiment, the body covering further comprises a manifold in fluid communication with the thermal fluid passages of the body covering. The manifold further comprising a thermal fluid inlet port configured to connect with the thermal fluid supply tube and a thermal fluid return port configured to connect with the thermal fluid return tube. The manifold further comprises one or more remote heating outlet ports and a remote heating return ports.

The system of one embodiment comprises one or more remote thermal loops. Each of the one or more thermal loops have a supply end and a return end, wherein the supply end is in fluid communication with one of the remote thermal outlet port and the return end is in fluid communication with one of the remote thermal return ports. The remote thermal loops are configured to deliver thermal fluid to a location on the patient that is remote from the body covering. For example, the remote thermal loops are affixed, in one embodiment to heating pads. The remote thermal heating loops are configured to be placed in thermal contact with a patient's hands, arms, feet, legs and or head. In one embodiment, there is a method that includes a step of heating one or more of a patient's hands, arms, feet, legs or head.

In one embodiment, the oxygen delivery interface is selected from the group comprising a respirator mask (such as a facial mask or a nasal mask) or a respirator tube (such as an oral breathing cannula or a nasal breathing cannula). Optionally, the oxygen delivery interface has a moisture capture filter configured to trap moisture exhaled from the patient and reintroduce moisture upon inhalation. Generally, the moisture capture filter is placed in a respirator mask.

In an embodiment, the oxygen delivery interface is in fluid communication with the oxygen delivery source by means of an oxygen delivery tube that is thermally regulated (ie, heated or cooled). In one embodiment, the oxygen delivery tube is thermally regulated by thermal fluid. In another embodiment, the oxygen delivery tube is thermally regulated in a heat exchange relationship with the heat exchanger. In another embodiment, the tube is heated by a heating element in heat exchange relationship with the oxygen delivery tube. There is also a method that includes the step of thermally regulating oxygen in the oxygen delivery tube.

In one embodiment, the one or more vital sign devices include each of a patient body temperature sensor, a patient oximeter; a patient heart rate monitor. The invention optionally includes the step of thermally regulating oxygen in the oxygen delivery tube.

In one embodiment, there is a portable microclimate and life-support system for care of a plurality of patients, comprising a portable housing that houses therein (i) a heat exchanger configured to regulate the temperature of a thermal fluid, wherein the heat exchanger has a plurality of thermal fluid outlet ports and a plurality of thermal fluid return ports, (ii) an oxygen source, (iii) a plurality of display units, wherein each display unit has one or more vital sign displays. The system further comprises a plurality of body coverings. Each body covering is configured to be placed in covering contact with one of the plurality of patients. Each body covering has a set of one or more thermal fluid passages to regulate the temperature of the patient in thermal contact with the each body covering.

The system further includes a plurality of thermal conduits. Each of the thermal fluid conduits is in fluid communication with one set of the one or more thermal fluid passages of the body covering. Furthermore, each of the thermal conduits have a thermal fluid supply tube in fluid communication with one of the thermal fluid outlet ports and a thermal fluid return tube in fluid communication with one of the thermal fluid inlet ports. Each of the thermal conduits form a closed fluid loop configured to deliver thermal fluid from the heat exchanger to a corresponding one or more thermal fluid passages and returning thermal fluid from the corresponding one or more thermal fluid passages.

The system further comprises a plurality of oxygen delivery interfaces corresponding to the plurality of patients. The system also includes a plurality of oxygen delivery conduits. Each of the plurality of oxygen delivery conduits are in fluid communication with an oxygen source configured to deliver oxygen from the oxygen delivery source to corresponding oxygen delivery interfaces.

The system optionally comprises a plurality of sets of one or more vital sign measurement devices selected from the group consisting of a patient body temperature sensor, a patient oximeter; a patient heart rate monitor, wherein the plurality of sets of one or more vital sign measurement devices is in electromagnetic communication with the plurality of display units.

The present invention is described hereinafter in Detailed Description of the Invention in reference to the drawings and examples, which are intended to teach, describe and exemplify one or more embodiments of the invention and is in no way intended to limit the scope of the invention.

BRIEF DESCRIPTION OF THE DRAWING

FIG. 2A is a perspective view of a microclimate cooling garment.

FIG. 2B is a perspective view of a microclimate cooling garment on a user.

DETAILED DESCRIPTION OF THE INVENTION

The present invention includes a portable microclimate and life-support system for care of a patient. In one embodiment, the system is referred to as a Medical Oxygen Thermal Hybrid System ("MOTHS") or Military Medical Oxygen Thermal Hybrid System ("MMOTHS"). These systems exemplify the present invention and integrate thermal heating and cooling capability with an oxygen supply (preferably a thermally regulated oxygen supply) and a patient monitoring feedback display into one single unit. MOTHS or MMOTHS and other systems of the present invention can be either powered from the console of vehicle or aircraft or portable with a battery (rechargeable or disposable) for treatment for civilian medical emergencies or US military combat casualty and trauma patients awaiting medical evacuation to a hospital.

Figure 1:
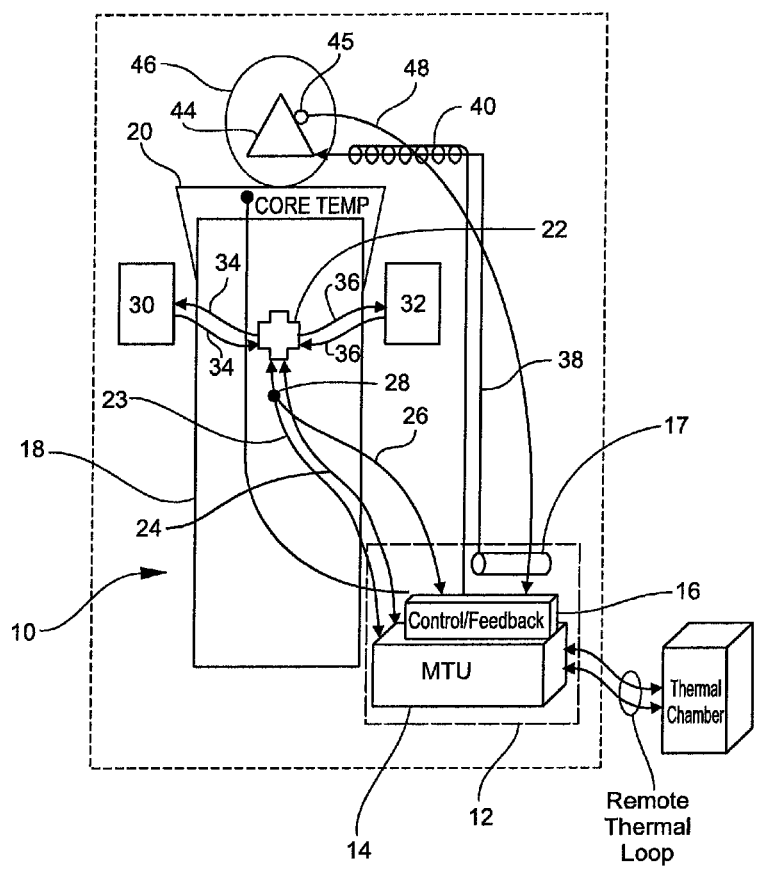
FIG. 1 is a schematic of a military medical oxygen thermal hybrid system of one embodiment of the present invention.

With reference to FIG. 1, there is a MMOTHS 10 according to one embodiment of the present invention. The MMOTHS 10 comprises a portable housing 12 shown schematically with broken lines. The portable housing houses a microclimate thermal unit. The microclimate thermal unit includes a heat exchanger and a power source (both not shown in FIG. 1). The portable housing includes a control panel and feedback unit 16. The control panel and feedback unit 16 displays the temperature of the thermal fluid in response to user inputs. The control panel and feedback unit 16 includes a display of patient's vital signs such as core temperature, blood oxygen levels, and heart rate (or pulse). It also includes without limitation the display of the temperature of oxygen delivered to the patient and the temperature of thermal fluid before entering the one or more thermal fluid passages (not shown in FIG. 1). The portable housing 12 also houses an oxygen tank 17 in one embodiment. The portable housing of one embodiment includes a place where a folded or rolled thermal blanket 18 can be placed. As shown schematically in FIG. 1, the blanket 18 covers the torso 20 of a patient. The blanket has a manifold 22. The manifold is in fluid communication with the heat exchanger of the MTU 14 via a thermal fluid supply tube 23 that delivers thermal fluid to the manifold 22 and a thermal fluid return tube 24 that returns thermal fluid from the manifold 22. Temperature of the thermal fluid in the thermal fluid supply tube is measured by a temperature sensor or temperature probe 28. The temperature probe 28 is connected to the control panel and feedback unit 16 via line 26. The manifold is in fluid communication with one or more thermal fluid passages (not shown in FIG. 1) within the blanket 18. The manifold 22 is also in fluid communication with remote thermal pads 30 and 32 that are supplied thermal fluid by a fluid loop 34 and 36 respectively. Oxygen is delivered from an oxygen delivery source (eg. oxygen tank 17) via an oxygen delivery conduit 38 to an oxygen delivery interface 44 (in one embodiment a respiratory face mask). Here the oxygen delivery interface fits over the face 46 (shown schematically). The temperature of the oxygen prior to delivery to the patient is measured by temperature sensor 45 affixed to the oxygen delivery interface 44. The electrical signal relating to the temperature sensor is communicated back to the control panel and feedback unit 16 via line 48. The oxygen delivery conduit 38 in one embodiment is heated by a heating coil 40 that covers at least a portion of the length of the oxygen delivery conduit 38.

The system of the present invention addresses the treatment or regulation of a patient's body temperature, the delivery of air or oxygen, and the regulation of one or more vital signs in an "all-in-one" system, and makes it available to the first responding medical personnel allowing them to treat or sustain life of the patient while awaiting transportation to a hospital. The system is lightweight and compact.

Optionally, the present invention can be used in a prophylactic capacity may include pilots, copilots, airmen or jumpers in extreme environments (hot, cold, high-altitude, or any combination thereof), alpine explorers and mountain climbers. Likewise, ground vehicle commanders, drivers, and crewmen in extreme hot or cold environments could benefit from using the system of the present invention. Prevention of hypothermia, hyperthermia and hypoxia will enhance the US war fighter's alertness, help prevent fatigue, and ultimately increase mission effectiveness.

The users of one or more systems of the present invention including a MOTHS or a MMOTHS fall into the treatment category may likely include civilian or US military heat stress (hyperthermia) casualties. This could benefit patients awaiting transport to a hospital via ambulance or aerial medical evacuation. Hyperthermia is a well known and documented problem in hot climates. The system of the present invention also features the ability to treat hypothermia (cold stress), as well as provide warmed inhaled medical oxygen. Alternatively it can provide warmed air or an oxygen-air mixture with an additional accessory.

Heating the inhaled oxygen or oxygen-air mixture provides heat to the user's torso internally. The system of the present invention can also provide simultaneous heating to the user's torso externally, by means of a liquid-circulating thermal blanket with localized thermal pad capability, which can be placed on extremities at the user's discretion. Heating of the torso can be more effective if performed by simultaneous external active temperature regulation (with a heating or cooling blanket) and internal temperature regulation (inhalation of temperature regulated gas. Cooling of the torso can also be performed in a similar manner utilizing the liquid-circulating thermal blanket with localized thermal pads. The pads house one or more thermal fluid passages that are in a heat exchange relationship with the surface of the pads. A thermal fluid is circulated through the thermal fluid passages in the pads to provide thermal regulation to objects that are placed in a heat exchange relationship with the thermal pads.

The system of the present invention has cooling capabilities that can optionally be utilized to keep blood bags, IV bags, drinking water, or other fluids chilled for transport in hot environments. In one embodiment, a thermal chamber is constructed with a remote thermal fluid loop that comprises one or more thermal fluid passages that are placed inside the thermal regulation chamber. The thermal fluid passages circulate thermal fluid in a heat exchange relationship with the matter inside the thermal chamber. In one embodiment, the thermal chamber is insulated and the thermal fluid passages align the inside of the thermal chamber. In one embodiment, the thermal regulation chamber is a foam insulated box such as a beverage cooler or the like.

In one embodiment, there is a method of cooling the content of a thermal regulation chamber by circulating thermal fluid that is cooler than the temperature inside the thermal regulation chamber. Blood bags, IV bags, drinking water or other fluids can be chilled for transportation in hot environments. Prior to infusion of a fluid into a patient such as blood or IV fluid, these fluids can be heated by passing a thermal fluid that is a temperature greater than the temperature of the infusion fluid—preferably the temperature of the fluid is heated close to body temperature prior to infusion.

In addition to treatment of patients in cold conditions, the cooling capabilities of the system according to one or more embodiments of the present invention can be employed to treat heat stress casualties by providing a cooled garment or blanket to patients in extreme hot environments such as, for example, the Iraqi or Afghan deserts in the summer.

In one embodiment, the system of one embodiment of the present invention (including a MOTHS or MMOTHS) provides the following capabilities: (a) heat stress relief, prevention of, or treatment of hyperthermia, to civilian or military personnel operating aircraft or ground vehicles, to passengers in aircraft or ground vehicles, or to dismounted personnel in hot environments; microclimate cooling to the user's torso externally by means of a cooling blanket, cooling pads, and/or cooling garments, which are worn or placed against or near the skin.

In MOTHS, the MTU is compatible with the existing US Army Microclimate Cooling Garment (MCG), such as NSN 8415-01-508-1512, fielded en masse on rotorcraft and ground vehicles. With reference to FIG. 2A and FIG. 2B, there is a vest 50 to cover the torso of a person 52 which in one embodiment is a patient. The vest has a front side 54 and a back side 55. The vest has one or more plurality of thermal fluid passages 58 mounted to the inside of the vest 50 on both the front side 54 and the back side 55 of the vest. The thermal fluid passages 58 are in fluid communication with the thermal conduit 56 of the vest 50. The thermal conduit having a thermal supply line and a thermal return line respectively connect to the inlet port and outlet port of the heat exchanger. The vest 50 is secured to the wearer 52 by shoulder straps 60 strapped between the neck 64 and the arms 62 of the wearer 52. A chest strap 66 fastens the front side 54 and the back side 55 under the arm 62. Waist straps 68 secure the vest 50 at the waist of the wearer 52.

Figure 3A:
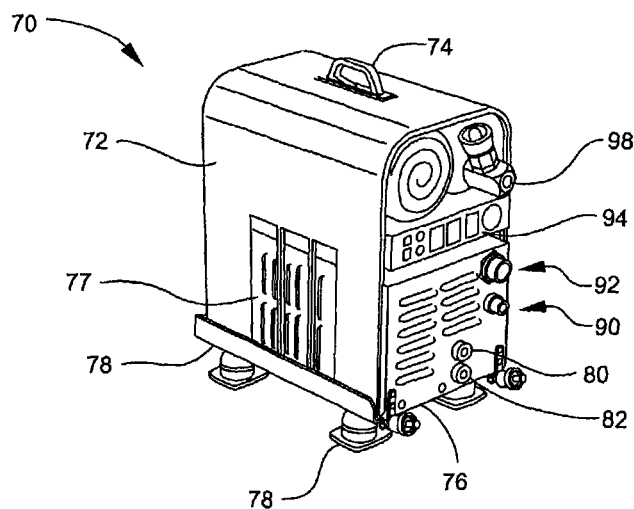
FIG. 3A is a perspective view of a military medical oxygen thermal hybrid system of one embodiment installed on a mounting tray.
Figure 3B:
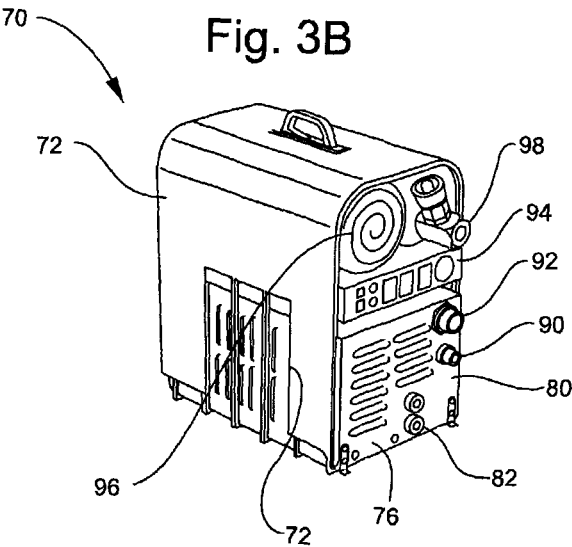
FIG. 3B is a perspective view of a military medical oxygen thermal hybrid system of one embodiment in man-portable mode.

MOTHS is designed to be fully compatible with existing and fielded US Army and US Marine mounting trays. As shown with reference to FIG. 3A, the portable housing 70 shows a protective exterior shell 72 for housing several components of the system of the present invention. The portable housing 70 has a handle 74 at the top. Optionally, backpack straps can be attached to one side of the MOTHS so that the device can be carried on the back. The portable housing 72 has a base 76. Optionally, the base is mounted on a mounting tray 78. Supported by the base 76 is the microclimate thermal unit 77 that contains the heat exchanger (not visible in FIGS. 3A and 3B). The heat exchanger is in fluid communication with a thermal fluid outlet port 80 (a thermal fluid supply) and a thermal fluid return port 82 (thermal fluid return). A temperature adjustment knob 90 is mounted to the portable housing 70. There is a connector 92 for main power. There is also a control/feedback display 94 that displays the one or more vital measurements of the patient such as core temperature, blood oxygen levels, heart rate (ie. pulse). The display is configured to optionally display the temperature of the thermal fluid in the thermal fluid supply line and the temperature of the oxygen.

The housing has a compartment for storing a body covering 96. Preferably, the body covering is a blanket that is rolled or folded into a compact size and placed in a hermetically sealed package. The housing also has a compartment for an oxygen supply 98. As shown, the oxygen supply 98 is an oxygen tank.

Figure 4:
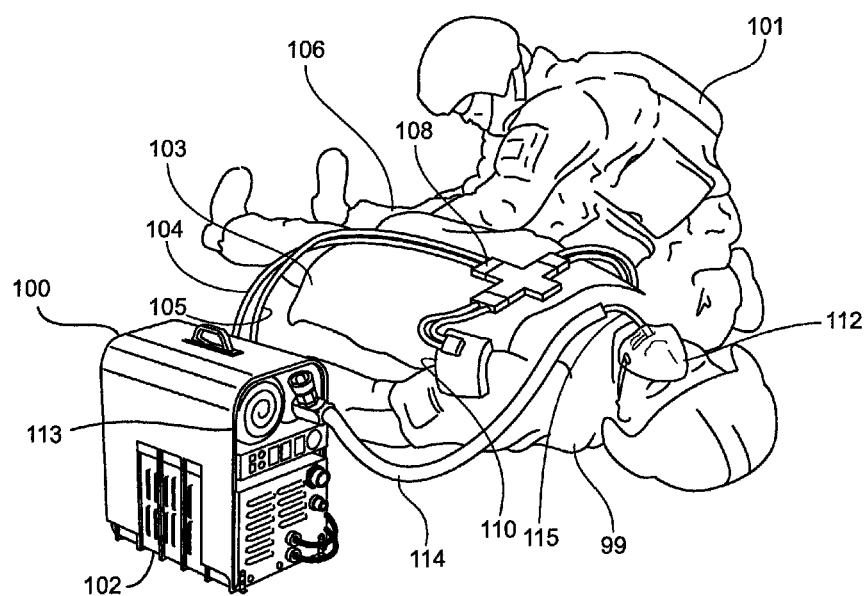
FIG. 4 is a diagram of a military medical oxygen thermal hybrid system deployed on a patient.

With reference to FIG. 4. The system of the present invention is shown in use by a medical personnel 101 treating a patient 99. The system comprises a portable housing 100 having a microclimate thermal unit 102 comprising a heat exchanger. Thermal fluid is supplied to a manifold 108 along thermal fluid conduit 104. The thermal fluid conduit 104 has a thermal fluid supply line 103 and thermal fluid return line 105. The manifold is in fluid communication with one or more thermal fluid passages that are affixed to the underside of the body covering 106 and supply thermal fluid to the patient for regulation of temperature. The manifold 108 is in fluid communication with a remote thermal loops 111 that deliver thermal fluid to remote thermal pads 110 for heating limbs and extremities of a patient such as hands, arms, feet, legs and head. Oxygen is delivered from an oxygen source 113 to an oxygen delivery interface 112 such as an oxygen delivery mask via an oxygen supply tube 115. The oxygen supply tube has a secondary oxygen warming sleeve 114. A heating coil in one embodiment heats the oxygen supply tube 115 under the secondary oxygen warming sleeve 114. Oxygen is delivered simultaneously as thermal fluid is delivered to regulate the temperature of a patient. In one embodiment warm thermal fluid is delivered in a heat exchange manner to the exterior of the patient to provide external active heating. Warmed oxygen is delivered to the respiratory system to provide internal active heating. When both occurs at the same time, recovery from hypothermia is more rapid.

One of the benefits of the present invention is preventing cold stress relief, prevention of, or treatment of hypothermia, to civilian or military personnel operating aircraft or ground vehicles, to passengers in aircraft or ground vehicles, or to dismounted personnel in cold environments.

The present invention features the ability to provide microclimate heating to the user's torso, both internally, through inhaled oxygen, air, or oxygen-air mixture, and also simultaneously externally, by means of a cooling blanket, cooling pads, and/or cooling garments, which are worn or placed against or near the skin. In one embodiment, the user has control over the temperature of the thermal fluid. The temperature can be adjusted to heat or cool slowly or rapidly at the discretion of the medical personnel.

In one embodiment the oxygen source comprises a compact pressurized oxygen storage vessel. The oxygen source can be a standard existing oxygen-generating equipment (OBOGS) or standard oxygen pressurized vessels.

In one embodiment, the present invention is a MOTHS that includes a thermal blanket and thermal pads/inserts.

In one embodiment, the present invention provides the user with monitoring, feedback and control capabilities. These can be used as physiological monitors for a patient, as feedback for user control, or to monitor and control the temperature of stored blood bags, IV bags or drinking water during transport. Control capabilities include the ability to increase or decrease the temperature of the thermal fluid and warm the breathing oxygen. Sensors with feedback include a pulse oximeter, inhaled oxygen temperature sensor or probe, an oxygen storage vessel pressure, a body temperature sensor or probe, a thermal fluid supply temperature sensor or probe.

In one embodiment, the present invention is a system for thermal regulation of a patient and providing oxygen delivery referred to in one embodiment as a MOTHS. MOTHS consists of the following integrated sub-systems: a microclimate thermal unit (MTU); a snug-fitting Microclimate Thermal Blanket (MTB) with integrated thermal pads; an insulated umbilical which connects the MTU with the MTB, by means of a manifold and liquid quick disconnect (LQDC); a pressurized oxygen storage vessel as an oxygen source; a regulated breathing ventilator (mask); an insulated umbilical which connects the oxygen storage vessel to the oxygen delivery mask, and features the ability to heat the inhaled gas; a control and feedback monitor that displays the vital signs of the patient.

MOTHS, one embodiment, is designed to be compatible with US Army Microclimate Cooling Garment (MCG) NSN 8415-01-508-1512; US Army mounting trays, such as P/N LSF00238-001; Standard existing oxygen generating equipment (OBOGS); standard existing oxygen or breathing air pressurized vessels; heat exchanger for blood bag, IV-bag, or drinking water cooling or heating.

Figure 5:
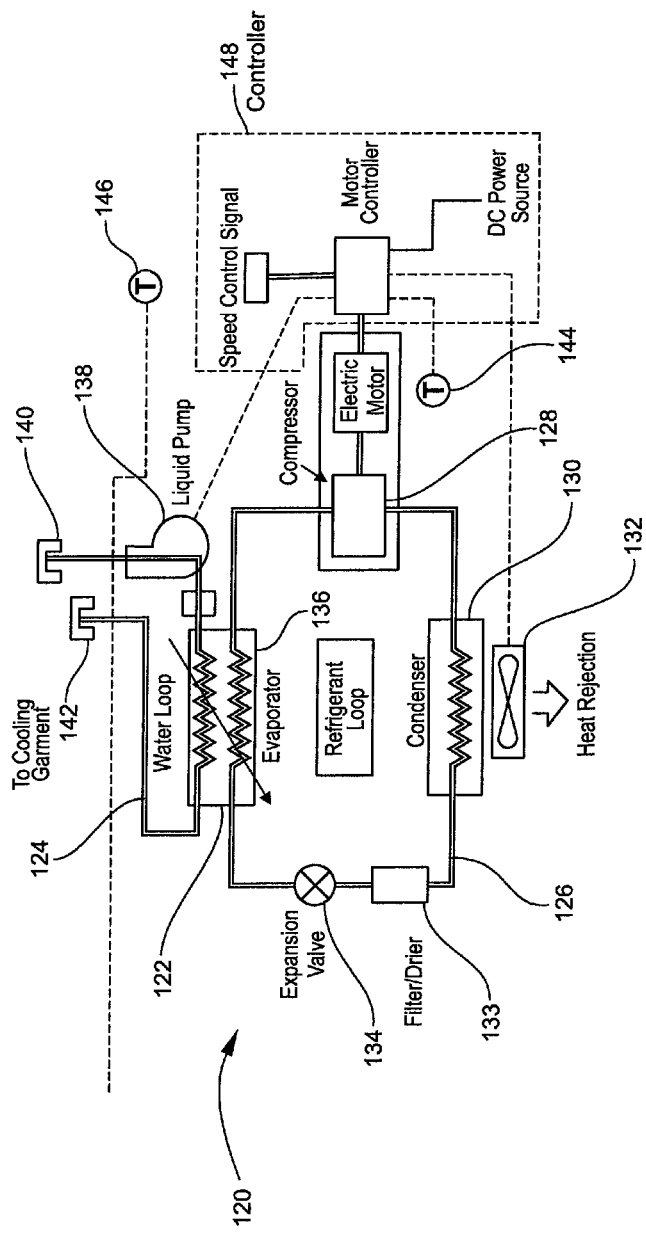
FIG. 5 is a schematic of a microthermal unit refrigeration and heating circuit schematic.

The microclimate thermal unit 120 utilizes an optimized vapor compression cooling cycle to cool a thermal fluid (a water/propylene glycol mixture). The system is described with reference to FIG. 5. In heating mode, a heater in the heat exchanger 122 is affixed to the condenser coils 136 converts electrical power into heat. The heater's coils are in close proximity with heat exchanger 122. The heat exchanger 122 warms the thermal fluid in the water/propylene glycol thermal fluid loop 124. The cooling circuit 126 utilizes refrigerant (R134a) in a standard vapor compression refrigeration cycle. A ruggedized, semi-hermetic, reciprocating piston type compressor 128 is utilized to compress the refrigerant vapor, increasing its pressure and temperature. The compressed refrigerant then passes through a condenser 130, where heat is removed and discharged to ambient surroundings by means of a fan 132 within the MTU. As heat is removed, the refrigerant experiences a decrease in temperature, causing it to condense into a liquid. This liquid remains at high pressure as it exits the condenser. It then passes through a filter/drier 133 and then through an expansion valve 134, flowing through a restriction (orifice) which causes a pressure drop and partial phase change of the refrigerant. Exiting the valve, the refrigerant is now a two phase mixture (vapor and liquid), which has a substantially reduced pressure and temperature. It is the boiling (evaporation) of this cold liquid phase which provides the majority of the system's cooling capability (a lesser amount is provided by the cold vapor phase as well). The last stop in the refrigeration loop before the process begins again at the compressor is the evaporator 136. As its name implies, this is where the evaporation of the cold liquid phase of the refrigerant takes place. The evaporator is part of the heat exchanger 122 in which the heat of the thermal fluid from the user's thermal blanket is transferred into the cold refrigerant. This results in a temperature drop of the thermal fluid, hence providing cooling of the fluid before it is circulated back to the user (a water pump 138 within the MTU circulates the thermal fluid to and from the user in a continuous manner). The thermal fluid passes through thermal fluid outlet port 140 and returns through a thermal fluid return port 142

In heating mode, the MTU receives an electrical signal from the user, turning off the compressor and fan, leaving only the water pump on. The power previously consumed by the fan and compressor (for refrigeration) is now diverted to a resistive electrical element for heating (not shown in FIG. 5). The resistive heating element is in close contact with the evaporator 136 of the heat exchanger 122 underneath the insulation. Heat is transferred into the thermal fluid, causing a rise in temperature. Dual sensors 144 and 146 monitor temperatures within the system to prevent scalding the user. The MTU features a controller, with built-in logic, control and test capabilities. It also has other useful functions, including power consumption optimization to maximize battery life in MOTHS portable mode. The MTU also provides automated thermal safety limits.

In either heating or cooling mode, the MTU pumps the heated or cooled thermal fluid through an insulated umbilical to the user. A manifold is utilized for this purpose which has multiple ports for plugging in accessories. These accessories include thermal blankets, thermal bags, hot or cold packs, or thermal garments. There is also an optional additional accessory available to cool or warm blood bags, IV bags, medicine, or drinking water supplies for transport.

The insulated umbilical features a bypass with a pressure-activated check valve. This allows the user to pre-cool the thermal fluid present in the in the system prior to hooking up to the system. When the system is turned on without a user being connected, the bypass allows the thermal fluid to circulate and get cool. The user then simply connects by means of a liquid quick disconnect (LQDC) after a few minutes. The thermal fluid solution circulates through the umbilical to the user as illustrated in FIG. 4. The thermal blanket or garment is worn by the user on the torso to either remove excess metabolic heat, or to warm, as previously described.

The MTU can operate in cooling mode and provide cooling in environments with ambient temperatures ranging from 55° F. to 150° F., while simultaneously surviving prolonged exposure to the high vibrations typical of military helicopters and military tracked vehicles. The system nominally provides 350 Watts of cooling at an ambient air temperature of 125° F. Similarly, the MTU can operate in heating mode and provide heating in environments with ambient temperatures ranging from 0° F. to 95° F. The system is designed to nominally provide 250 Watts of heating at 0° F. to the thermal fluid, and 100 Watts of heating to the inhaled gas.

Integrated into MOTHS is an oxygen supply system consisting of a pressurized oxygen vessel, a valve, regulator, hose and medical mask. The oxygen can be heated as well, by means of resistive heating using electrical power. In this manner, warm oxygen can be provided to the user or patient.

MOTHS utilizes a compact pressurized (2100 psig) oxygen vessel which is approximately 1 liter in volume. MOTHS is designed to also be compatible with larger pressurized oxygen vessels and OBOGS systems which may be present on certain aircraft, vehicles, MEDEVACS and ambulances. An adapter is needed for connection with these devices.

Physiological oxygen need is dependent on altitude and breathing rate. A full MOTHS oxygen bottle is designed to have a duration of approximately one hour for a patient needing typical supplemental medical oxygen flow at sea level (at an oxygen flow rate of 2.5 LPM). Duration is dependent on flow rate. For example, at a light supplemental medical oxygen consumption rate of 0.5 LPM, the duration would be 5 hrs. Likewise, higher flow rates will shorten the duration.

The oxygen delivery mask of one embodiment is a common medical type facemask. The mask is held in place by a lightweight elastic headband, which allows the mask to be removed quickly. The mask is a delivery device that supplies oxygen from the pressurized storage vessel to the user's lungs. It allows approximately 40% oxygen to be delivered to the user, and is intended to be used in conditions where a person cannot breath on his own, or else cannot draw sufficient amounts of oxygen into his lungs.

An insulated umbilical transports the oxygen to the user's mask. Underneath the insulation is a resistive heating element which utilizes electrical power to warm the oxygen if so desired by the user. This can be turned ON or OFF by the user.

An additional accessory is available which can be utilized to draw ambient air into the oxygen stream, resulting in an oxygen-air mixture. Alternatively, the user can choose to draw in only ambient air (without supplemental oxygen). The user can then warm the inhaled gas if desired.

A user control/patient monitoring and feedback unit is integrated into MOTHS. The unit is connected to sensors which monitor and give feedback of key vital signs. This provides the means to monitor and regulate the temperature of the thermal fluid, to turn on or off the heating of the inhaled gas, to monitor and regulate the temperature of the inhaled gas, to monitor the patient's pulse-ox, and to monitor the patient's body temperature.

The unit is designed to operate on aircraft or vehicle-supplied 28 VDC power, or alternatively on 24 VDC battery-supplied power. The unit is designed to meet all of the requirements of MIL-STD-704 (aircraft power requirements) as well as MIL-STD-1275 (ground vehicle power requirements) and as such can withstand the associated power and voltage fluctuations and variances.

MOTHS is designed to operate under vehicle or aircraft supplied power supplied at 28 VDC, or alternatively at 24 VDC under battery power when used in man-portable mode.

For vehicular or airborne use or transport, MOTHS is easily installed by hand into a mounting tray which is hard-mounted to the vehicle or aircraft platform. A power cable supplies aircraft or vehicle power while the battery pack recharges. See FIG. 3A. Using this approach, the mounting tray and power cable are secured to the airframe or vehicle platform and considered 'A-Kit' hardware, while the MOTHS could be considered removable 'B-Kit' hardware. The US Army and US Marines often utilize such an approach.

For man-portable mode, the aircraft or vehicle power cable is disconnected, and the battery cable is connected in its place. The MOTHS then disconnects easily by hand in seconds from its mounting tray. See FIG. 3B.

To utilize MOTHS heating or cooling capabilities, the user simply turns it on in the desired mode (HEAT or COOL), and then connects the Liquid Quick Disconnect Connector (LQDC) fitting on his thermal blanket or thermal garment to the mating LQDC on the insulated umbilical on the MOTHS. The LQDC chosen for MOTHS is a proven design which facilitates emergency egress with a moderate breakaway force. If the user needs to exit the aircraft or vehicle quickly, the umbilical will detach at the LQDC with an applied pull force of 7-20 lbs without having to press the disconnect button. The LQDC complies with US Army Performance Specification AVNS-PRF-10174, has been qualified by the US Army.

As previously described, the thermal fluid may be pre-cooled or pre-warmed by turning on the system and letting it run for a few minutes prior to the user connection being made. A bypass check valve within the umbilical makes this possible. Once the user is connected to the MOTHS and receiving either warmed or cooled thermal fluid to his blanket or garment, he may start to feel too cold or too hot. This, of course, will depend on ambient environmental conditions and the patient's own metabolic heat generation rate. If this does occur, the user can increase or turn down the heating or cooling effect by simply adjusting a control knob.

If the user needs oxygen, the oxygen can be delivered under heated conditions as well by simply switching on the OXYGEN HEAT mode on MOTHS Control and Feedback Display unit.

The Control and Feedback Display unit provides readouts (feedback) from the body temperature sensor, the pulse-ox sensor, the supply thermal fluid temperature, and the oxygen temperature sensor. Thermal safety limits are built in to MOTHS to prevent scalding thermal fluid or oxygen which is too hot to inhale. However, other than these built in safety limits, it is at the user's discretion to control the thermal fluid and oxygen temperatures.

Figure 6:
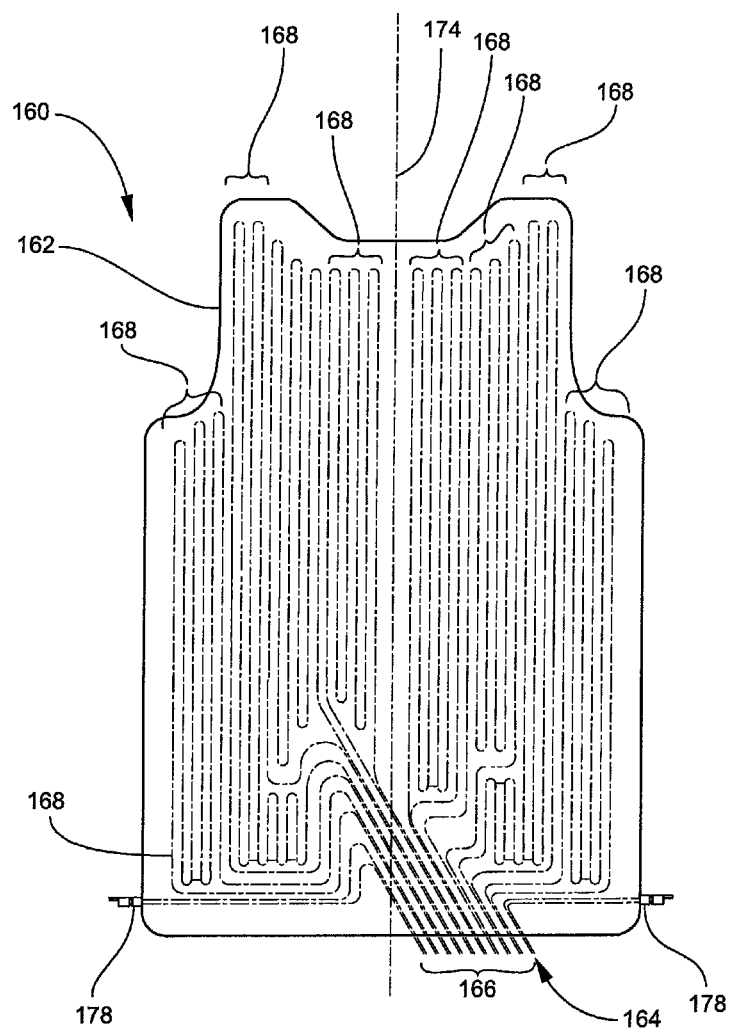
FIG. 6 is a diagram of a blanket according to one embodiment of the invention.

With reference to FIG. 6, a body covering of one embodiment is described. The body covering is blanket assembly 160 that is made of a blanket 162 that is of woven or nonwoven fabric. The blanket 162 is preferably somewhat elastic. The elasticity helps the blanket 162 conform closely to the patient's shape. In one embodiment, the blanket 162 is made of cotton-polyester blend. Another embodiment features a Nomex-PBI blended material. The more snug the fit between the patient and the blanket, the more efficient the thermal regulation. Thus, the blanket design is key to efficient operation of the system of the present invention.

The blanket assembly 160 comprises a manifold 164 having a plurality of inlet and outlet ports 166. One or more fluid passages 168 are attached to one or more pairs of inlet and outlet ports 166. In one embodiment, there are a minimum of six inlet ports and six outlet ports. In another embodiment, there are preferably ten inlet ports and ten outlet ports. The fluid passages 168 are flexible tubes that are laid out in close proximity to maximize the surface area of the blanket that is covered by the one or more fluid passages 168. The tubes need to be pliable and have favorable thermal conductivity properties.

In one embodiment, the tubes forming the fluid passages 168 are made of polyvinyl chloride (PVC) tubing. In one embodiment, the outer diameter of the fluid passages is a minimum of 3/32 inch and a maximum of 1/8 inch, preferably an outer diameter of 5/32 inch. The space between the fluid passages is a maximum of 1/2 inch. In one embodiment, it is advantageous to fold the blanket into a compact package and hermetically seal the blanket. Therefore, having a single fold line 174 medial to the blanket and rolling the blanket after the single fold will minimize kinking when the tubes are oriented at an angle that is less than 60 degrees from the fold line 174, preferably less than 45 degrees from the fold line 174 and most preferably at 30 degrees from the fold line. The blanket can be folded and the individual tubes will twist upon folding rather than bend or kink.

The manifold of one embodiment has a plurality of remote thermal loops 178. The remote thermal loops 178 deliver thermal fluid to the extremity of the loop. In one embodiment, the loop is attached to a remote thermal pad that is configured to heat limbs or extremities of a patient such as feet, legs, arms, hands or head.

Medical Oxygen Thermal Hybrid System consists of seven primary parts—the microclimate Thermal Unit (MTU), the umbilical, the manifold, the thermal accessories, an oxygen supply system, an oxygen warmer, and a control/feedback monitor.

The MTU uses a basic vapor compression cycle which produces a cooling effect of the coolant fluid (a water/propylene glycol mixture). The MTU pumps the cooled fluid through an umbilical to a manifold which has multiple ports for plugging in accessories. These accessories include thermal blankets, thermal bags, cold packs, thermal garments, or an insulated chamber to be used for cooling, storing and preserving IV bags, blood, medicines, etc. The heating may alternatively be generated by electrical coil.

Integrated into the MOTHS unit is an oxygen supply system consisting of an oxygen tank, valve, regulator, hose and mask. The oxygen can be warmed through use of either the warm coolant or through an electric coil to provide warmed oxygen to the patient.

The control/feedback unit is integrated into the MOTHS unit as a means to regulate the temperature of the cooling fluid. The controller contains sensors to monitor and report critical vital signs including oxygen concentration, oxygen temperature and body temperature.

The thermal accessories are yet to be developed, but are based in theory and practice on the MCU cooling garment.

MOTHS provides vehicle mounted or man portable heating, cooling, and oxygen source for combat casualty and trauma patients with a patient monitoring display in a single self contained unit.

MOTHS will utilize MTU technology which is similar to the microclimate cooling unit ("MCU") of which over 18,000 MCU units that have been fielded in ground vehicles and aircraft to date, but with the additional heating feature and with additional thermal accessories.

MOTHS, optionally, utilizes oxygen life support systems that are known in commercial and military aircraft, space vessels, and optionally a parachutist high altitude oxygen system (PHAOS).

The umbilical includes and improves upon MCU umbilical technology that is known in the art.

What is claimed is:

1. A portable microclimate and life-support system for care of a patient, comprising:
    a portable housing that houses therein (i) a heat exchanger configured to regulate the temperature of a thermal fluid, wherein the heat exchanger has a thermal fluid outlet port and a thermal fluid return port, (ii) an oxygen source, (iii) one or more vital sign displays;
    a body covering including a manifold, the body covering configured to be placed in covering contact with the patient and having one or more thermal fluid passages to regulate the temperature of the patient in thermal contact with the body covering;
    a thermal conduit configured to be in fluid communication with the one or more thermal fluid passages of the body covering via the manifold, the thermal conduit having a thermal fluid supply tube configured to be in fluid communication with the thermal fluid outlet port of the heat exchanger and a thermal fluid return tube configured to be in fluid communication with the thermal fluid return port of the heat exchanger, wherein the thermal conduit, when in fluid communication with the thermal fluid passages, thermal fluid supply tube, and thermal fluid return tube, forms a closed fluid loop for delivering thermal fluid from the heat exchanger to the one or more thermal fluid passages and returning thermal fluid from the one or more thermal fluid passages;
    the manifold including a thermal fluid inlet port configured to connect with the thermal fluid supply tube, a thermal fluid return port configured to connect with the thermal fluid return tube, one or more remote thermal regulation outlet ports, and one or more remote thermal regulation return ports, at least one of the remote thermal regulation outlet ports and at least one of the remote thermal regulation return ports configured to connect to the thermal fluid passages of the body covering;
    an oxygen delivery interface;
    an oxygen delivery conduit in fluid communication with the oxygen source configured to deliver oxygen from the oxygen delivery source to the oxygen delivery interface; and
    one or more vital sign measurement devices selected from the group consisting of a patient body temperature sensor, a patient oximeter, and a patient heart rate monitor, wherein the one or more vital sign measurement devices is in electromagnetic communication with the one or more vital sign displays.

2. The system of claim 1, further comprising a thermal fluid temperature sensor configured to measure the thermal fluid temperature prior to the thermal fluid entering the one or more thermal fluid passages of the thermal cover, wherein the thermal fluid temperature is displayed in a thermal temperature display on the portable housing.

3. The system of claim 2, further comprising an oxygen temperature sensor configured to measure the oxygen temperature in or upstream from the oxygen delivery interface entering the one or more fluid passages, wherein the thermal fluid temperature is displayed in a thermal temperature display on the portable housing.

4. The system of claim 1, wherein the housing is configured to be carried by one person using a handle attached to the portable housing.

5. The system of claim 1, wherein the housing is configured to be carried on a person's back.

6. The system of claim 1, wherein the portable housing has a maximum weight of about 60 pounds.

7. The system of claim 1, wherein the portable housing is less than 1.5 cubic feet.

8. The system of claim 1, wherein the body covering is made of an elastic fabric material and further comprises fasteners configured to fasten the body covering to the patient.

9. The system of claim 1, wherein the body covering is a blanket or clothing garment.

10. The system of claim 1, further comprising:
    one or more remote thermal regulation loops, wherein each of the one or more thermal regulation loops has a supply end and a return end, wherein the supply end is configured to connect to one of the remote thermal regulation outlet ports of the manifold and the return end is configured to connect to one of the remote thermal regulation return ports of the manifold.

11. The system of claim 10, further comprising one or more remote thermal pads, the remote thermal pads configured to be in fluid communication with the manifold by connecting to the one or more thermal regulation loops.

12. The system of claim 1, wherein the oxygen delivery interface is selected from the group comprising a respirator mask or a respirator tube.

13. The system of claim 1, wherein the oxygen delivery interface is in fluid communication with the oxygen delivery source by an oxygen delivery conduit that is heated.

14. The system of claim 13, wherein the oxygen delivery conduit is heated by an electric coil.

15. The system of claim 1, wherein the one or more vital sign devices include each of a patient body temperature sensor, a patient oximeter, and a patient heart rate monitor.

16. The system of claim 1, wherein the oxygen source is at least in part oxygen from ambient air.

17. The system of claim 1, wherein the oxygen source is at least in part from an oxygen air tank.

18. The system of claim 1, wherein the thermal conduit includes liquid quick disconnect connections and a thermal bypass with a pressure-activated check valve configured to allow heating or cooling of the system before connecting the body covering.

19. A method of therapeutically or prophylactically treating a patient for hypothermia, and at the same time therapeutically or prophylactically treating a patient for a condition selected from the group consisting of hyperventilation, shock or hypoxia, wherein the method comprising the steps of:
    providing a system of claim 1;
    delivering heated thermal fluid to the plurality of thermal fluid passages of the body covering thereby providing active heat to the skin of the patient;

delivering oxygen from the oxygen source to the respiratory system of the patient; and monitoring one or more vital signs of the patient.

20. A method of therapeutically or prophylactically treating a patient for hyperthermia and at the same time therapeutically or prophylactically treating a patient for a condition selected from the group consisting of hyperventilation, shock or hypoxia, wherein the method comprising the steps of:

providing a system of claim 1;

delivering cooled thermal fluid to the plurality of thermal fluid passages of the body covering thereby providing active heat to the skin of the patient;

delivering oxygen from the oxygen source to the respiratory system of the patient; and monitoring one or more vital signs of the patient.

21. A portable microclimate and life-support system for care of a plurality of patients, comprising:

a portable housing that houses therein (i) a heat exchanger configured to regulate the temperature of a thermal fluid, wherein the heat exchanger has a plurality of thermal fluid outlet ports and a plurality of thermal fluid return ports, (ii) an oxygen source, (iii) a plurality of display units, wherein each display unit has one or more vital sign displays;

a plurality of body coverings each including a manifold, wherein each body covering is configured to be placed in covering contact with one of the plurality of patients, wherein each body covering has a set of one or more thermal fluid passages to regulate the temperature of the patient in thermal contact with the each body covering;

a plurality of thermal conduits, wherein each of the thermal fluid conduits are configured to be in fluid communication with one set of the one or more thermal fluid passages of the body covering via a corresponding manifold of the body covering, wherein each of the thermal conduits has a thermal fluid supply tube configured to be in fluid communication with one of the thermal fluid outlet ports of the heat exchanger and a thermal fluid return tube configured to be in fluid communication with one of the thermal fluid return ports of the heat exchanger, wherein each of the thermal conduits, when in fluid communication with the thermal fluid passages, thermal fluid supply tube, and thermal fluid return tube, forms a closed fluid loop configured to deliver thermal fluid from the heat exchanger to a corresponding one or more thermal fluid passages and return thermal fluid from the corresponding one or more thermal fluid passages;

each manifold including a thermal fluid inlet port configured to connect with the corresponding thermal fluid supply tube, a thermal fluid return port configured to connect with the corresponding thermal fluid return tube, one or more remote thermal regulation outlet ports, and one or more remote thermal regulation return ports, at least one of the remote thermal regulation outlet ports and at least one of the remote thermal regulation return ports configured to connect to the corresponding thermal fluid passages of the body covering;

a plurality of oxygen delivery interfaces corresponding to the plurality of patients;

a plurality of oxygen delivery conduits, wherein each of the plurality of oxygen delivery conduits are in fluid communication with the oxygen source configured to deliver oxygen from the oxygen delivery source to corresponding the oxygen delivery interfaces; and a plurality of sets of one or more vital sign measurement devices selected from the group consisting of a patient body temperature sensor, a patient oximeter, and a patient heart rate monitor, wherein the plurality of sets of one or more vital sign measurement devices is in electromagnetic communication with the plurality of display units.

* * * * *